(12) United States Patent
Roe (10) Patent No.: US 7,227,472 B1
(45) Date of Patent: Jun. 5, 2007

(54) MULTISTAGE SAFETY SCREENING OF EQUIPMENT OPERATORS

(76) Inventor: Kevin Roe, 4975 Moorpark Ave., San Jose, CA (US) 95129

( * ) Notice: Subject to any disclaimer, the term of this patent is extended or adjusted under 35 U.S.C. 154(b) by 213 days.

(21) Appl. No.: 11/143,830

(22) Filed: Jun. 2, 2005

(51) Int. Cl.
G08B 23/00 (2006.01)
B32B 5/02 (2006.01)
G01N 1/22 (2006.01)

(52) U.S. Cl. .................. 340/576; 340/573.1; 340/632; 422/84; 180/272; 600/532

(58) Field of Classification Search ............... 340/500, 340/576; 422/84; 73/23.3
See application file for complete search history.

(56) References Cited

U.S. PATENT DOCUMENTS

| 3,811,116 | A | | 5/1974 | Takeuchi et al. |
| 3,823,382 | A | | 7/1974 | Gaddy |
| 4,093,945 | A | * | 6/1978 | Collier et al. ............... 180/272 |
| 4,592,443 | A | | 6/1986 | Simon |
| 4,613,845 | A | | 9/1986 | DuBois |
| 4,738,333 | A | | 4/1988 | Collier et al. |
| 4,926,164 | A | * | 5/1990 | Porter et al. ................ 340/576 |
| 4,996,161 | A | | 2/1991 | Conners et al. |
| 5,793,292 | A | | 8/1998 | Ivey, Jr. et al. |
| 5,969,615 | A | | 10/1999 | Ivey, Jr. et al. |
| 6,620,108 | B2 | * | 9/2003 | Duval et al. ................ 600/532 |
| 6,748,301 | B1 | | 6/2004 | Ryu |
| 6,886,653 | B1 | | 5/2005 | Bellehumeur |
| 2002/0084130 | A1 | | 7/2002 | Der Ghazerian et al. |

\* cited by examiner

*Primary Examiner*—Donnie L. Crosland
(74) *Attorney, Agent, or Firm*—Kevin Roe (57) ABSTRACT

Methods and systems to screen equipment operators for impairments, such as intoxication, physical impairment, medical impairment, or emotional impairment, to selectively test the equipment operators and control the equipment if impairment of the equipment operator is determined. One embodiment is a method to screen an equipment operator for intoxication. A second embodiment is a method to screen an equipment operator for impairment, such as intoxication, physical impairment, medical impairment, or emotional impairment. A third embodiment is an equipment operator screening system to determine impairment, such as intoxication, physical impairment, medical impairment, or emotional impairment.

20 Claims, 6 Drawing Sheets

MULTISTAGE SAFETY SCREENING OF EQUIPMENT OPERATORS

BACKGROUND OF THE INVENTION

1. Field of the Invention

This invention relates generally to controlling the operation of equipment by dangerous operators, and more specifically to controlling the operation of equipment by operators who cannot satisfy a multistage screening for intoxication or other impairment.

2. Description of the Prior Art

Intoxicated or otherwise impaired equipment operators (e.g., physically impaired, medically impaired, or emotionally impaired operators) of equipment (e.g., automobiles, trucks, industrial vehicles, public transportation vehicles, such as buses, trains, planes, and ships, and dangerous machinery in general) needlessly continue to cause many thousands of horrible deaths and injuries each year around the world. The main focus of previous efforts has been alcohol intoxication of vehicle operators, since this continues to be the most prevalent type of dangerous operator impairment. Though systems have been devised that disable a vehicle based on an operator's alcohol level, such systems have been too complex, and have not been employed as they are usually too expensive, too annoying for an operator to tolerate on a daily basis, and/or simply too easy for an operator to circumvent. Some systems have used coordination measurement that requires the user to push buttons in a random order within a given amount of time in order to allow the vehicle to be started. Other systems have used detectors for analyzing the breath of the vehicle operator in order for the operator to start a vehicle.

U.S. Pat. No. 6,886,653 issued to Bellehumeur, on May 3, 2005, discloses a system including a galvanic skin sensor that can provide trans-dermal monitoring of a person's skin for ascertaining whether or not the person has consumed alcohol and the person's skin temperature. The sensor is connected through an actuating switch control system that is mounted electrically, typically within the vehicle ignition system that can act as a cutoff switch based on the various inputs from the trans-dermal sensor. The nature of this system appears likely to limit its use, but the disclosures of this patent are hereby incorporated by reference.

U.S. Pat. No. 6,748,301 issued to Ryu, on Jun. 8, 2004, discloses an apparatus and method for prevention of driving of motor vehicle under the influence of alcohol and prevention of vehicle theft, in which a voice and a voice secret code of an authorized driver is stored by learning through a voice recognition apparatus and microphone mounted in the vehicle, and then the breath of an intended operator is detected when the driver says the secret code to check whether or not the operator is legally drunk, and also the intended operator's voice secret code is compared to the stored voice and voice secret code. The driver is allowed to start the vehicle only when the operator is not legally drunk and the voice secret code matches the stored voice secret code. The nature of this system appears likely to limit its use, but the disclosures of this patent are hereby incorporated by reference.

U.S. patent application No. 20020084130 published by Der Ghazarian, et al., on Jul. 4, 2002, discloses a voice recognition breathalyzer comprising a microphone for transducing spoken expression into electronic signals and a breathalyzer sensor for transducing breath content into electronic signals. It includes an audio and breathalyzer sensor circuit for conditioning the electronic signals from the microphone and breathalyzer sensor; a memory storage for storing speech templates and toxic breath setting; a processor for processing the conditioned electronic signals and for simultaneously comparing the processed, conditioned electronic signals with the speech templates and the toxic breath setting threshold stored in the memory storage, generating a unique signal when the processed, conditioned electronic signals are substantially similar to one of the speech templates and below the toxic breath setting threshold. The nature of this system appears likely to limit its use, but the disclosures of this patent application are hereby incorporated by reference.

U.S. Pat. No. 5,969,615 issued to Ivey Jr., et al., on Oct. 19, 1999, discloses a system for monitoring and covering the use of a hand-operated machine by an impaired individual through detection of toxins in the individual. This system uses vapor from an individual's hands drawn through a sampling apparatus. The resultant signal is used to estimate the alcoholic content of the individual. The nature of this system appears likely to limit its use, but the disclosures of this patent are hereby incorporated by reference.

U.S. Pat. No. 5,793,292 issued to Ivey Jr., on Aug. 11, 1998, discloses a device to prevent hand operated machines from being operated by an impaired individual by measuring toxins in the person using sensors that interact with the vehicle. The nature of this system appears likely to limit its use, but the disclosures of this patent are hereby incorporated by reference.

U.S. Pat. No. 4,996,161 issued to Conners, et al., on Feb. 26, 1991, discloses a breath alcohol testing system that may be used in conjunction with a vehicle. Although the breathanalyzer may be highly accurate, its interaction with a vehicle that requires a person to breathe into a facemask is likely to annoy the operator. The nature of this system appears likely to limit its use, but the disclosures of this patent are hereby incorporated by reference.

U.S. Pat. No. 4,738,333 issued to Collier, et al., on Apr. 19, 1988, discloses a sobriety interlock system that prevents a vehicle or other equipment from being started unless the identity of a designated operator is confirmed by the system and the operator passes a breath sobriety test. The designated operator is trained to perform a physical act, the successful completion of which can be determined by the system and which requires at least a predetermined number, N, of attempts to learn. A necessary precondition for starting the vehicle is satisfied when the system determines that the identity-confirming act has been performed in fewer than N attempts. The nature of this system appears likely to limit its use, but the disclosures of this patent are hereby incorporated by reference.

U.S. Pat. No. 4,613,845 issued to DuBois, on Sep. 23, 1986, discloses an apparatus for preventing operation of machinery by an intoxicated operator, using an alcohol sensor located near the control panel on a portion of the steering wheel. The nature of this system appears likely to limit its use, but the disclosures of this patent are hereby incorporated by reference.

U.S. Pat. No. 4,592,443 issued to Simon, on Jun. 3, 1986, discloses a sobriety interlock that includes an apparatus for detecting alcohol on the breath that is connected to the ignition system of a vehicle. The nature of this system appears likely to limit its use, but the disclosures of this patent are hereby incorporated by reference.

U.S. Pat. No. 3,823,382 issued to Gaddy, on Jul. 9, 1974, discloses a system for inhibiting motor vehicle operation by intoxicated drivers. This device uses a breath-analyzer that measures the alcohol level using a chemical reaction in order to prevent the car from starting. The nature of this system appears likely to limit its use, but the disclosures of this patent are hereby incorporated by reference.

U.S. Pat. No. 3,811,116 issued to Takeuchi, et al., on May 14, 1974, discloses a device for detecting mental impairment in a driver that includes a degree of fatigue or drunkenness, judging the mental ability of the operator for operating a vehicle. The nature of this system appears likely to limit its use, but the disclosures of this patent are hereby incorporated by reference.

While many of the systems in the prior art cleverly and impressively attempt to solve the problem of preventing a person who is intoxicated from operating a vehicle, the systems typically can still be circumvented by accident or by intent. Furthermore, these systems usually cannot detect the physically impaired, medically impaired, or emotionally impaired operators if they are otherwise sober. And due to their time-consuming or intrusive nature, they are usually likely to annoy an operator to such an extent as to motivate the operator to do whatever is necessary to intentionally circumvent the system, defeating the entire initial purpose of the system. Furthermore, any one prior art system alone can experience a likelihood of incorrectly detecting operator intoxication or impairment when the operator is not intoxicated or impaired (i.e., a false positive), or incorrectly missing operator intoxication or impairment when the operator is truly intoxicated or otherwise truly impaired (i.e., a false negative).

What is needed is a system that overcomes these problems by using a multistage screening approach to minimize the annoyance to an operator and increase the probability of correctly controlling the operation of equipment by a truly intoxicated or otherwise truly impaired operator.

SUMMARY OF THE INVENTION

The present invention overcomes the problems of the prior art by using a multistage screening approach to minimize the annoyance to an operator and increase the probability of controlling the operation of equipment (e.g., automobiles, trucks, industrial vehicles, public transportation vehicles, such as buses, trains, planes, and ships, and dangerous machinery in general) by a truly intoxicated or otherwise truly impaired operator. Embodiments of the invention can be implemented in numerous ways. Three aspects of the invention are described below.

A first aspect of the invention is directed to a method to screen an equipment operator for intoxication. The method includes measuring at least one type of chemical in the air in proximity to an equipment operator, wherein the at least one type of chemical is associated with intoxication; selectively testing the equipment operator when the at least one type of chemical is detected at a sufficient level to indicate intoxication of the equipment operator; and controlling the operation of the equipment if the selective testing of the equipment operator indicates intoxication of the equipment operator.

A second aspect of the invention is directed to a method to screen an equipment operator for impairment. The method includes measuring the level of at least one type of sound frequency in proximity to an equipment operator, wherein the at least one type of sound frequency is associated with impairment; selectively testing the equipment operator when the at least one type of sound frequency is detected at a sufficient level to indicate impairment of the equipment operator; and controlling the operation of the equipment if the selective testing of the equipment operator indicates the impairment of the equipment operator.

A third aspect of the invention is directed to an equipment operator screening system. The system includes a sound meter to measure the power level of at least one type of sound frequency in proximity to an equipment operator, wherein the at least one type of sound frequency is associated with impairment; a screening module to selectively test the equipment operator when the at least one type of sound frequency is detected at a sufficient power level to indicate impairment of the equipment operator; and a control module to control the operation of the equipment if the selective testing of the equipment operator by the screening module indicates the impairment of the equipment operator.

DETAILED DESCRIPTION OF THE PREFERRED EMBODIMENT

The primary goal of any embodiment of the present invention is to control the operation of equipment by an equipment operator when there is a very high probability that there is equipment operator impairment, such as intoxication (e.g., alcohol intoxication, chemical intoxication, or equivalent conditions), physical impairment (e.g., sudden injury, blindness, lack of air, poisonous or disabling gases or dusts, or equivalent conditions), medical impairment (e.g., stroke, diabetic coma, or equivalent conditions), or emotional impairment (e.g., grief, anger, psychosis, anxiety, or equivalent conditions). Due to the great inconvenience, any practical embodiment must have a very low probability of false positives (i.e., controlling/preventing the operation of equipment by an equipment operator because of an incorrect determination of impairment, such as intoxication, physical impairment, medical impairment, or emotional impairment). Due to the great danger, any practical embodiment must also have a very low probability of false negatives (i.e., allowing an impaired equipment operator to operate the equipment because of an incorrect determination of non-impairment). A multistage screening of the equipment operator for impairment will increase the accuracy of the screening and decrease both the probability of a false positive and a false negative.

Various embodiments of the invention are possible, but one embodiment method includes measuring at least one type of chemical (e.g., ethanol, or any other regulated mind-impairing chemical, such as cannabis, amphetamines, cocaine, and equivalents) in the air in proximity to an equipment operator, wherein the at least one type of chemical is associated with intoxication; and selectively testing the equipment operator when the at least one type of chemical is detected at a sufficient level to indicate intoxication of the equipment operator.

One embodiment of the invention also includes measuring at least one characteristic of the equipment operator that is associated with impairment, such as intoxication, physical impairment, medical impairment, or emotional impairment. Depending of the results of the measurement of at least one characteristic of the equipment operator, selective testing of the equipment operator can further determine whether the equipment operator is truly impaired and control operation of the equipment. The selective testing of the equipment operator can either require the active participation and knowledge of the equipment operator, or can be done without the active participation and knowledge of the equipment operator. The selective testing of the equipment operator can also increase in extent if the initial testing indicates possible impairment, such as intoxication, physical impairment, medical impairment, or emotional impairment.

Embodiments of the invention can be constructed from various combinations of screening modules to selectively measure various characteristics of an equipment operator. The screening modules can measure a characteristic of the equipment operator, such as a chemical in the breath of the equipment operator, electrical resistance of a portion of skin of the equipment operator, electrical conductivity of a portion of skin of the equipment operator, temperature of a portion of skin of the equipment operator, one or more optical characteristics of at least one eye of the equipment operator, optical response to at least one stimulus of at least one eye of the equipment operator, at least one speech characteristic of the equipment operator, comparison of at least one speech characteristic of the equipment operator to a sample speech characteristic of the equipment operator, a speed of dexterity of the equipment operator in performing at least one task, and a consistency of dexterity of the equipment operator in performing at least one task.

One embodiment of the invention also includes selective testing that selectively changes according to other factors chosen from factors, such as air temperature, oxygen levels, carbon dioxide levels, presence of gases, air humidity, air pressure, time of day, time duration of vehicle parking, voice loudness levels in proximity to the equipment, history of operation of the equipment by the equipment operator, initial beginning of operation of the equipment by the equipment operator, and ongoing operation of the equipment by the equipment operator. In other words, one embodiment of the invention can screen the operator for impairment, such as intoxication, physical impairment, medical impairment, or emotional impairment acquired during the operation of the equipment, not just impairments already existing at the initial beginning of operation of the equipment.

Controlling the operation of equipment by an impaired equipment operator can include many possible types of control responses. Controlling the operation of the equipment can include one or more of the following control responses: disabling the equipment, disabling the equipment after a time delay, temporarily disabling the equipment for a pre-selected time duration, shutting off power to the equipment, limiting the operation of the equipment to a lower speed of operation, limiting the operation of the equipment to allow only the return the equipment to a pre-selected state or a pre-selected location, denying entry to the equipment, activating an alarm, sending a warning message to another entity for assistance, issuing a warning message to the impaired equipment operator, and/or requesting another equipment operator replace the impaired equipment operator and then restricting equipment operation if the request is not obeyed within a pre-selected time.

Figure 1:
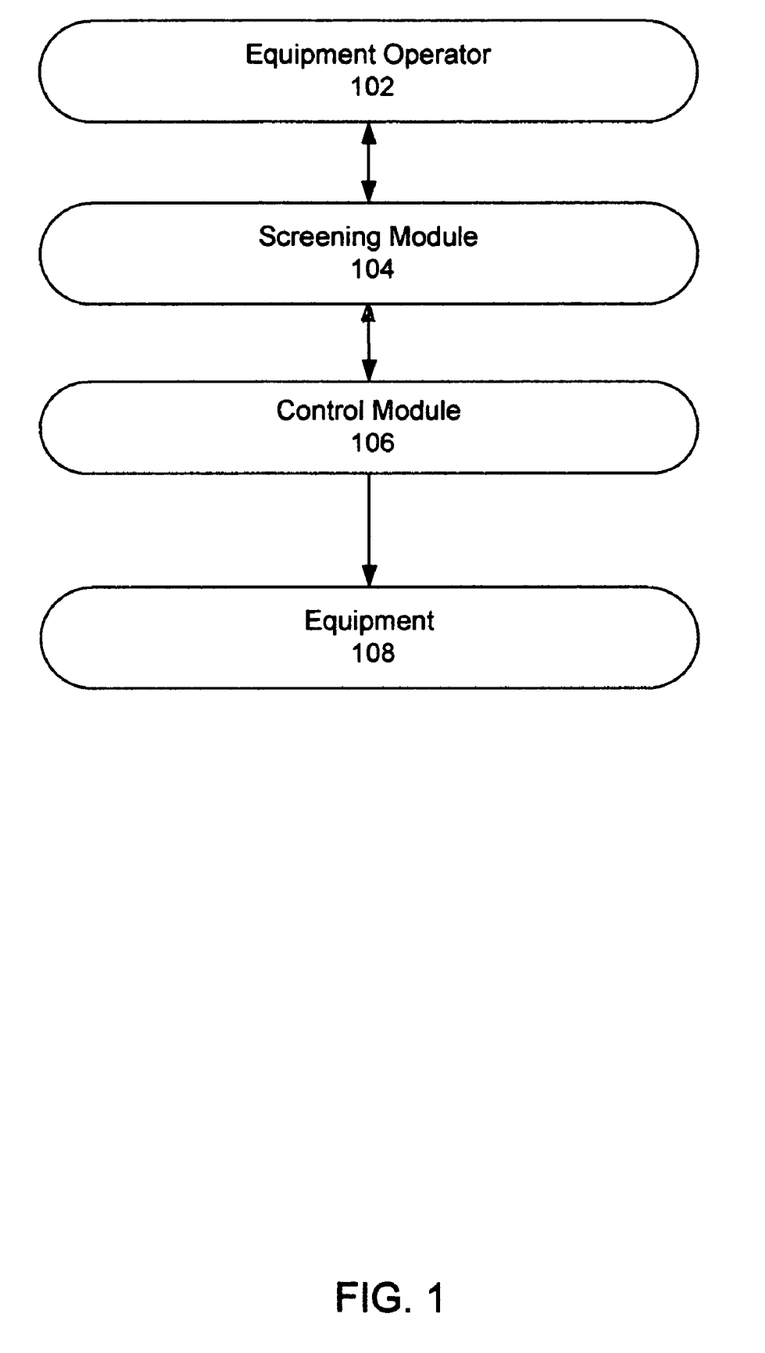
FIG. 1 illustrates a module diagram of a system to screen an equipment operator, in accordance with one embodiment of the invention.

FIG. 1 illustrates a module diagram of a system to screen an equipment operator, in accordance with one embodiment of the invention. The screening module 104 screens equipment operator 102 to determine at least one type of impairment. In one embodiment, the screening module 104 includes one or more commercially available test systems (computerized or non-computerized) that are readily available to screen, measure, or test humans or environments for unusual phenomena. In an alternative embodiment, the screening module 104 includes part or all of one or more of the intoxication detection systems taught in the prior art patents that have been previously listed and incorporated by reference. The screening module 104 determines whether the equipment operator 102 is impaired and whether to activate the control module 106. Control module 106 controls the equipment 108, using one or more of the control responses already listed above. For example, in one embodiment the control module 106 restricts operation of equipment 108 without delay, but in another embodiment the control module 106 restricts equipment 108 after a message is provided to the equipment operator 102 requesting another equipment operator, restricting operation after such a request is not obeyed with a pre-selected time.

Figure 2:
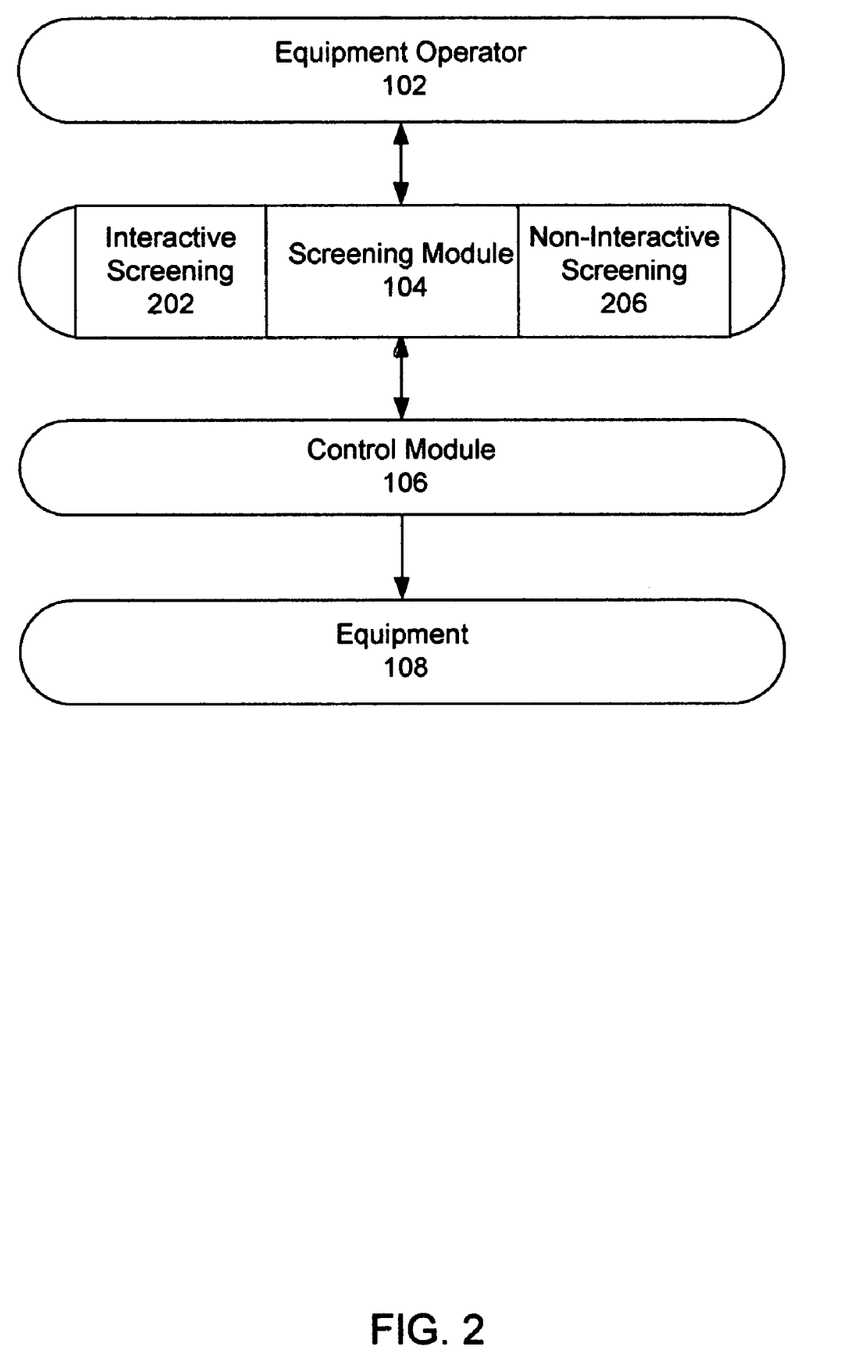
FIG. 2 illustrates a module diagram of a system to screen an equipment operator, in accordance with one embodiment of the invention.

FIG. 2 illustrates a module diagram of a system to screen an equipment operator, in accordance with one embodiment of the invention. The screening module 104 screens equipment operator 102 for some impairment, such as intoxication, physical impairment, medical impairment, or emotional impairment. The screening module 104 determines whether the equipment operator 102 is impaired and whether to activate the control module 106. Control module 106 controls the equipment 108, using one or more of the control responses listed above. In this embodiment of the invention, screening module 104 includes both interactive screening module 202 (which will screen the equipment operator 102 with the conscious interaction and awareness of the equipment operator 102) and non-interactive screening module 206 (which will screen the equipment operator 102 without the conscious interaction and awareness of the equipment operator 102). Non-interactive screening modules can measure a characteristic of the equipment operator, such as a chemical in proximity to the equipment operator, electrical resistance of a portion of skin of the equipment operator, electrical conductivity of a portion of skin of the equipment operator, temperature of a portion of skin of the equipment operator, one or more optical characteristics of at least one eye of the equipment operator, optical response to at least one stimulus of at least one eye of the equipment operator, at least one speech characteristic of the equipment operator, comparison of at least one speech characteristic of the equipment operator to a sample speech characteristic of the equipment operator, a speed of dexterity of the equipment operator in performing at least one task, and a consistency of dexterity of the equipment operator in performing at least one task. Interactive screening modules can ask the equipment operator to perform some task, such as speaking or physically moving some body part (e.g., hands or fingers) of the equipment operator.

Figure 3:
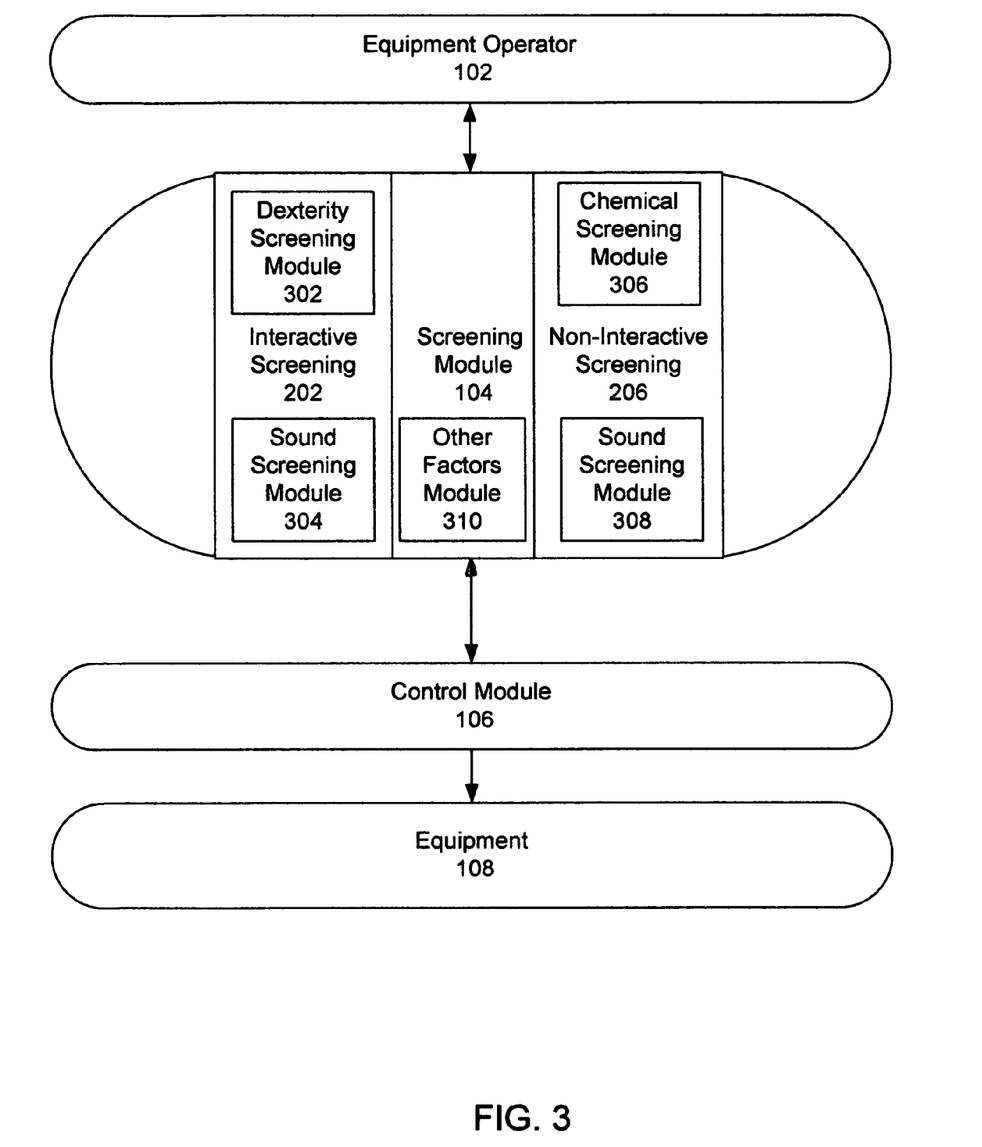
FIG. 3 illustrates a module diagram of a system to screen an equipment operator, in accordance with one embodiment of the invention.

FIG. 3 illustrates a module diagram of a system to screen an equipment operator, in accordance with one embodiment of the invention. The screening module 104 screens the equipment operator 102 for impairment, such as intoxication, physical impairment, medical impairment, or emotional impairment with a legally controlled chemical (or even a new chemical not yet legally regulated which is determined to impair the equipment operator). The screening module 104 determines whether the equipment operator 102 is impaired and whether to activate the control module 106. Control module 106 controls the equipment 108, using one or more of the control responses listed above. In this embodiment of the invention, screening module 104 includes both interactive screening module 202 (which will screen the equipment operator 102 with the conscious interaction and awareness of the equipment operator 102) and non-interactive screening module 206 (which will screen the equipment operator 102 without the conscious interaction and awareness of the equipment operator 102). Interactive screening module 202 includes dexterity screening module 302 and sound screening module 304. Non-interactive screening module 206 includes chemical screening module 306 and sound screening module 308. One or both of the interactive screening module 202 and non-interactive screening module 206 can also access other factors module 310 which can include other relevant data to consider with the screening results in determining whether there is a true impairment of the equipment operator. Other factors module 310 can selectively provide data on other factors, such as air temperature, air humidity, air pressure, time of day, time duration of vehicle parking, voice loudness levels in proximity to the equipment, history of operation of the equipment by the equipment operator, initial beginning of operation of the equipment by the equipment operator, and ongoing operation of the equipment by the equipment operator.

Figure 4:
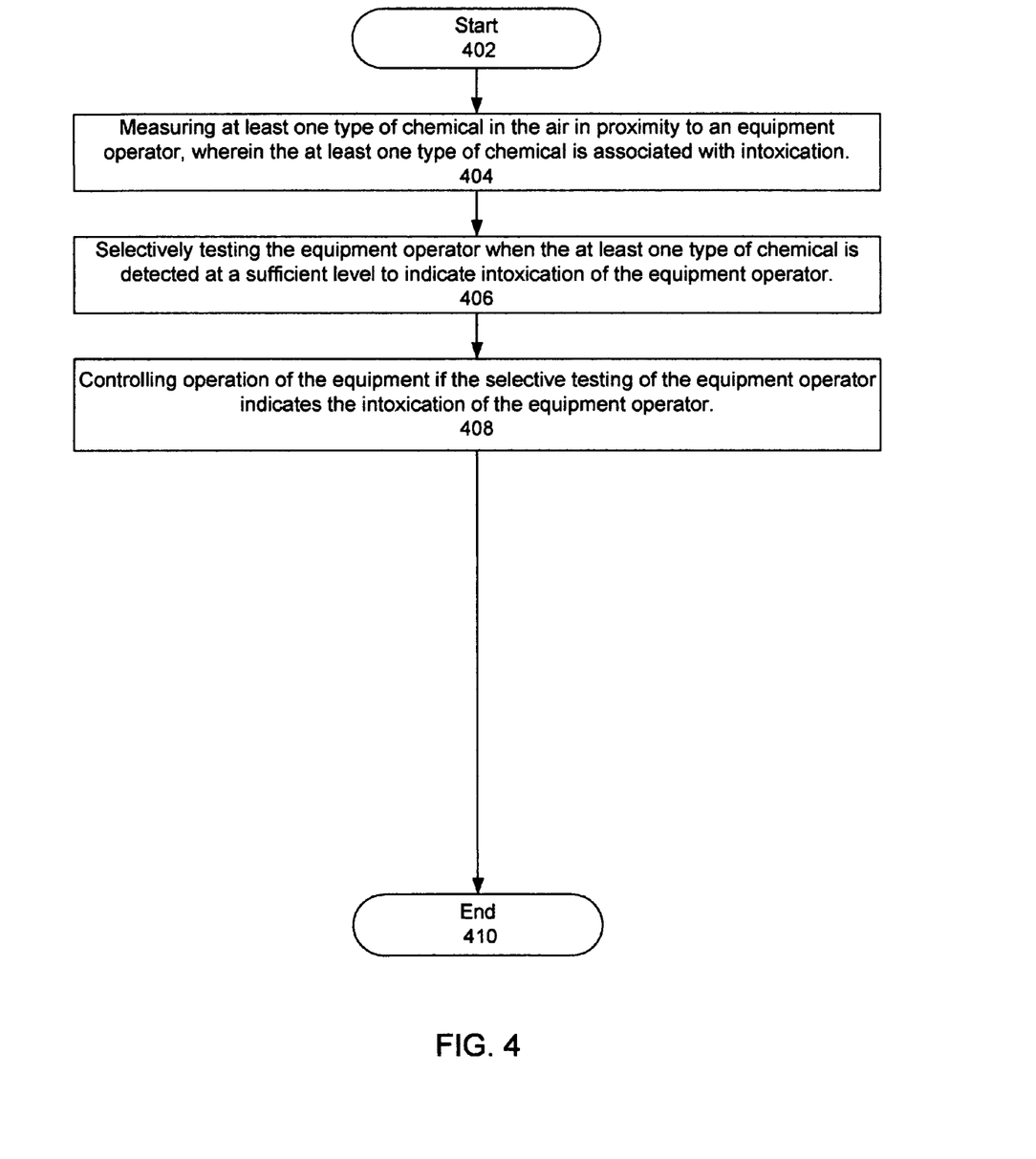
FIG. 4 illustrates a flowchart to screen an equipment operator, in accordance with another embodiment of the invention.

FIG. 4 illustrates a flowchart to screen an equipment operator, in accordance with another embodiment of the invention. The method starts in operation 402. Operation 404 is next and includes measuring at least one type of chemical in the air in proximity to an equipment operator. Operation 406 is next and includes selectively testing the equipment operator when the at least one type of chemical is detected at a sufficient level to indicate intoxication of the equipment operator. Operation 408 is next and includes controlling the operation of the equipment if the selective testing of the equipment operator indicates the intoxication of the equipment operator. Controlling the operation of the equipment can include one or more of the following control responses: disabling the equipment, disabling the equipment after a time delay, temporarily disabling the equipment for a pre-selected time duration, shutting off power to the equipment, limiting the operation of the equipment to a lower speed of operation, limiting the operation of the equipment to allow only the return the equipment to a pre-selected state or a pre-selected location, sending a warning message to another entity for assistance, issuing a warning message to the operator, and/or requesting another equipment operator replace the impaired equipment operator and then disabling the equipment if the request is not obeyed within a short time. The method ends in operation 410.

Figure 5:
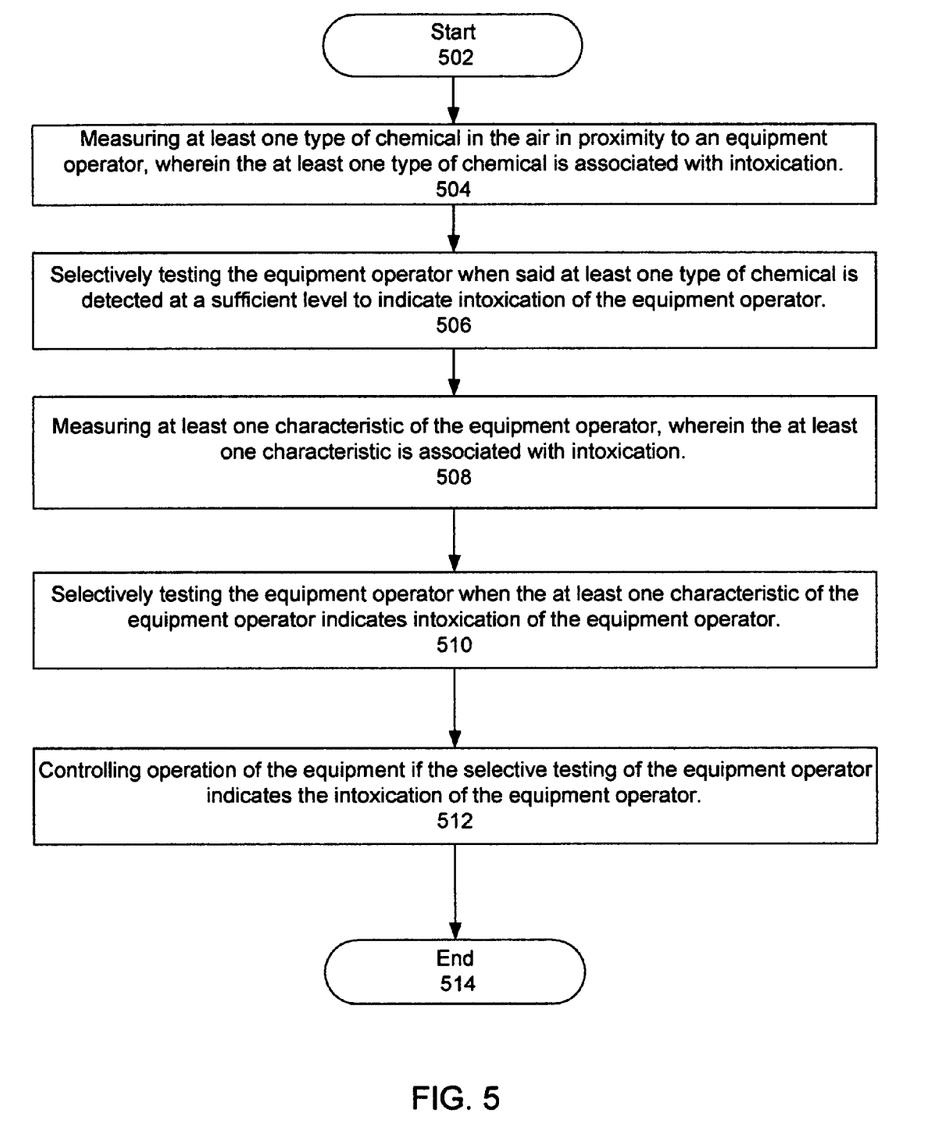
FIG. 5 illustrates a flowchart to screen an equipment operator, in accordance with one embodiment of the invention.

FIG. 5 illustrates a flowchart to screen an equipment operator, in accordance with one embodiment of the invention. The method starts in operation 502. Operation 504 is next and includes measuring at least one type of chemical in the air in proximity to an equipment operator. Operation 506 is next and includes selectively testing the equipment operator when the at least one type of chemical is detected at a sufficient level to indicate intoxication of the equipment operator. Operation 508 is next and includes measuring at least one characteristic of the equipment operator, wherein the at least one characteristic is associated with intoxication. Operation 510 is next and includes selectively testing the equipment operator when at least one characteristic of the equipment operator indicates the intoxication of the equipment operator. Operation 512 is next and includes controlling the operation of the equipment if the selective testing of the equipment operator indicates the intoxication of the equipment operator. The controlling operation can include one or more of the control responses listed above. The method ends in operation 514.

Figure 6:
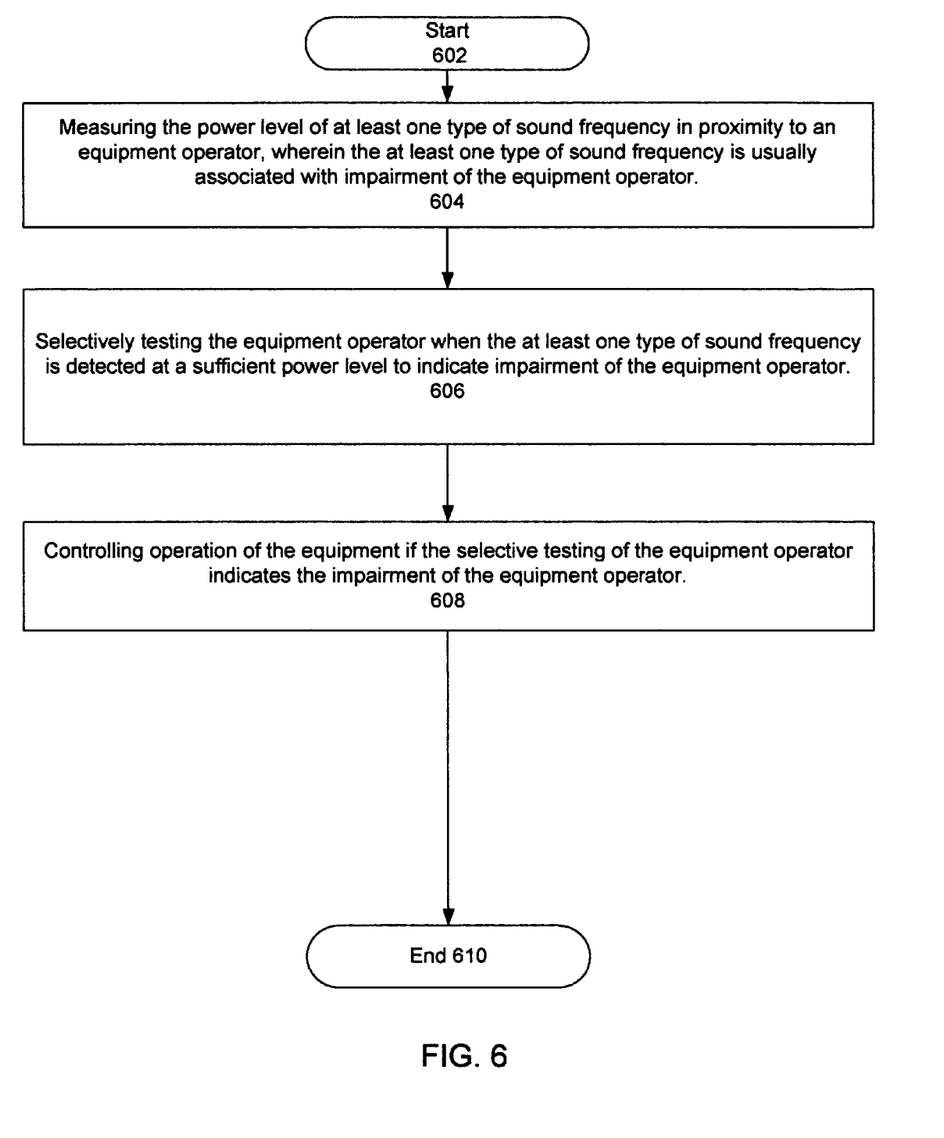
FIG. 6 illustrates another flowchart to screen an equipment operator, in accordance with one embodiment of the invention.

FIG. 6 illustrates another flowchart to screen an equipment operator, in accordance with one embodiment of the invention. The method starts in operation 602. Operation 604 is next and includes measuring the power level of at least one type of sound frequency in proximity to an equipment operator, wherein the at least one type of sound frequency is usually associated with impairment of the equipment operator. Operation 606 is next and includes selectively testing the equipment operator when the at least one type of sound frequency is detected at a sufficient power level to indicate impairment of the equipment operator. The sound frequency may be inside or outside the normal audio range of human hearing in various embodiments. Operation 608 is next and includes controlling the operation of the equipment if the selective testing of the equipment operator indicates the impairment of the equipment operator. The controlling operation can include one or more of the control responses listed above. The method ends in operation 610.

Other embodiments of the invention are possible. For example, other factors could be considered in screening the equipment operator, such as shaking of the equipment, sudden starts and stops of the equipment, or wild fluctuations in the operation of the equipment. Commercial motion detectors or microphones can be used for detection. Another embodiment can deny operator entry through the doors of enclosed equipment (e.g., autos, campers, recreational vehicles, trains, ships, airplanes, and so forth).

The exemplary embodiments described herein are for purposes of illustration and are not intended to be limiting. For example, when elements of "one embodiment" are disclosed, this does not imply the elements must be incorporated in "all embodiments." Therefore, those skilled in the art will recognize that other embodiments could be practiced without departing from the scope and spirit of the claims set forth below.

What is claimed is:

1. A method to screen an equipment operator for intoxication, comprising:
measuring at least one type of chemical in the air in proximity to an equipment operator, wherein said at least one type of chemical is associated with intoxication;
selectively testing said equipment operator when said at least one type of chemical is detected at a sufficient level to indicate intoxication of said equipment operator; and
controlling operation of said equipment if said selective testing of said equipment operator indicates said intoxication of said equipment operator.

2. The method of claim 1, further comprising:
measuring at least one characteristic of said equipment operator, wherein said at least one characteristic is associated with intoxication; and
selectively testing said equipment operator when said at least one characteristic of said equipment operator indicates intoxication of said equipment operator.

3. The method of claim 2, wherein said measuring at least one characteristic of said equipment operator includes measuring one or more characteristics selected from the group consisting of: at least one chemical in proximity to said equipment operator, blood pressure of said equipment operator, pulse rate of said equipment operator, electrical resistance of a portion of skin of said equipment operator, electrical conductivity of a portion of skin of said equipment operator, temperature of a portion of skin of said equipment operator, one or more optical characteristics of at least one eye of said equipment operator, optical response to at least one stimulus of at least one eye of said equipment operator, at least one speech characteristic of said equipment operator, comparison of at least one speech characteristic of said equipment operator to a reference speech characteristic of said equipment operator, a speed of dexterity of said equipment operator in performing at least one task, and a consistency of dexterity of said equipment operator in performing at least one task.

4. The method of claim 1, wherein said selective testing includes at least one test requiring an active participation by said equipment operator.

5. The method of claim 1, wherein said controlling operation of said equipment includes one or more control responses selected from the group of control responses consisting of: disabling said equipment, disabling said equipment after a time delay, temporarily disabling said equipment for a pre-selected time duration, shutting off power to said equipment, limiting operation of said equipment to a lower speed of operation, limiting the operation of said equipment to allow only return of said equipment to a pre-selected state, limiting the operation of said equipment to allow only return of said equipment to a pre-selected location, denying entry to said equipment, activating an alarm, sending a warning message to another entity for assistance, issuing a warning message to an impaired equipment operator, and making a request for another equipment operator to replace an impaired equipment operator and then restricting operation of said equipment if said request is not obeyed within a pre-selected time.

6. The method of claim 1, wherein said selective testing increases selective testing if initial testing indicates possible intoxication of said equipment operator.

7. The method of claim 1, wherein said selective testing selectively changes according to one or more other factors chosen from the group of factors consisting of air temperature, oxygen level, carbon dioxide level, presence of one or more gases, air humidity, air pressure, time of day, time duration of vehicle parking, voice loudness levels in proximity to said equipment, history of operation of said equipment by said equipment operator, initial beginning of operation of said equipment by said equipment operator, and ongoing operation of said equipment by said equipment operator.

8. A method to screen an equipment operator for impairment, comprising:
measuring the power level of at least one type of sound frequency in proximity to an equipment operator, wherein said at least one type of sound frequency is usually associated with impairment of said equipment operator;
selectively testing said equipment operator when said at least one type of sound frequency is detected at a sufficient power level to indicate impairment of said equipment operator; and
controlling operation of said equipment if said selective testing of said equipment operator indicates said impairment of said equipment operator.

9. The method of claim 8, wherein said impairment of said equipment operator includes intoxication of said equipment operator.

10. The method of claim 8, wherein said impairment of said equipment operator includes physical impairment of said equipment operator.

11. The method of claim 8, further comprising:
measuring at least one characteristic of said equipment operator, wherein said at least one characteristic is associated with impairment of said equipment operator; and
selectively testing said equipment operator when said at least one characteristic of said equipment operator indicates impairment of said equipment operator.

12. The method of claim 11, wherein said measuring at least one characteristic of said equipment operator includes measuring one or more characteristics selected from the group consisting of: at least one chemical in proximity to said equipment operator, blood pressure of said equipment operator, pulse rate of said equipment operator, electrical resistance of a portion of skin of said equipment operator, electrical conductivity of a portion of skin of said equipment operator, temperature of a portion of skin of said equipment operator, one or more optical characteristics of at least one eye of said equipment operator, optical response to at least one stimulus of at least one eye of said equipment operator, at least one speech characteristic of said equipment operator, comparison of at least one speech characteristic of said equipment operator to a reference speech characteristic of said equipment operator, a speed of dexterity of said equipment operator in performing at least one task, and a consistency of dexterity of said equipment operator in performing at least one task.

13. The method of claim 8, wherein said selective testing includes at least one test not requiring an active participation of said equipment operator.

14. The method of claim 8, wherein said controlling operation of said equipment includes one or more control responses selected from the group of control responses consisting of: disabling said equipment, disabling said equipment after a time delay, temporarily disabling said equipment for a pre-selected time duration, shutting off power to said equipment, limiting operation of said equipment to a lower speed of operation, limiting the operation of said equipment to allow only return of said equipment to a pre-selected state, limiting the operation of said equipment to allow only return of said equipment to a pre-selected location, denying entry to said equipment, activating an alarm, sending a warning message to another entity for assistance, issuing a warning message to an impaired equipment operator, and making a request for another equipment operator to replace an impaired equipment operator and then restricting operation of said equipment if said request is not obeyed within a pre-selected time.

15. The method of claim 8, wherein said selective testing includes more selective testing if initial testing indicates possible impairment of said equipment operator.

16. The method of claim 8, wherein said selective testing selectively changes according to one or more other factors chosen from the group of factors consisting of: air temperature, oxygen level, carbon dioxide level, presence of one or more gases, air humidity, air pressure, time of day, time duration of vehicle parking, voice loudness levels in proximity to said equipment, history of operation of said equipment by said equipment operator, initial beginning of operation of said equipment by said equipment operator, and ongoing operation of said equipment by said equipment operator.

17. An equipment operator screening system, comprising:
   a sound meter to measure the power level of at least one type of sound frequency in proximity to an equipment operator, wherein said at least one type of sound frequency is associated with impairment;
   a screening module to selectively test said equipment operator when said at least one type of sound frequency is detected at a sufficient power level to indicate impairment of said equipment operator; and
   a control module to control operation of said equipment if said selective testing of said equipment operator by said screening module indicates said impairment of said equipment operator.

18. The system of claim 17, wherein said control module to control operation of said equipment uses one or more control responses selected from the group of control responses consisting of: disabling said equipment, disabling said equipment after a time delay, temporarily disabling said equipment for a pre-selected time duration, shutting off power to said equipment, limiting operation of said equipment to a lower speed of operation, limiting the operation of said equipment to allow only return of said equipment to a pre-selected state, limiting the operation of said equipment to allow only return of said equipment to a pre-selected location, denying entry to said equipment, activating an alarm, sending a warning message to another entity for assistance, issuing a warning message to an impaired equipment operator, and making a request for another equipment operator to replace an impaired equipment operator and then restricting operation of said equipment if said request is not obeyed within a pre-selected time.

19. The system of claim 17, wherein said impairment of said equipment operator includes intoxication of said equipment operator.

20. The system of claim 17, wherein said screening module includes at least one module to measure at least one characteristic of said equipment operator selected from the group of characteristics consisting of: at least one chemical in proximity to said equipment operator, electrical resistance of a portion of skin of said equipment operator, blood pressure of said equipment operator, pulse rate of said equipment operator, electrical conductivity of a portion of skin of said equipment operator, temperature of a portion of skin of said equipment operator, one or more optical characteristics of at least one eye of said equipment operator, optical response to at least one stimulus of at least one eye of said equipment operator, at least one speech characteristic of said equipment operator, comparison of at least one speech characteristic of said equipment operator to a reference speech characteristic of said equipment operator, a speed of mechanical dexterity of said equipment operator in performing at least one task, and a consistency of mechanical dexterity of said equipment operator in performing at least one task.

* * * * *